US012653573B2

(12) United States Patent
Kalhorn et al.

(10) Patent No.: US 12,653,573 B2
(45) Date of Patent: Jun. 16, 2026

(54) MINIMALLY INVASIVE SUBDURAL EVACUATING SYSTEM

(71) Applicant: MUSC Foundation for Research Development, Charleston, SC (US)

(72) Inventors: Stephen Kalhorn, Mount Pleasant, SC (US); Ryan Kellogg, Charleston, SC (US); Joe Ruscito, Southport, CT (US)

(73) Assignee: MUSC Foundation for Research Development, Charleston, SC (US)

( * ) Notice: Subject to any disclaimer, the term of this patent is extended or adjusted under 35 U.S.C. 154(b) by 82 days.

(21) Appl. No.: 18/907,834

(22) Filed: Oct. 7, 2024

(65) Prior Publication Data

US 2025/0025206 A1 Jan. 23, 2025

Related U.S. Application Data

(60) Division of application No. 17/376,645, filed on Jul. 15, 2021, now Pat. No. 12,108,965, which is a continuation of application No. 16/917,166, filed on Jun. 30, 2020, now Pat. No. 11,065,033.

(60) Provisional application No. 62/869,653, filed on Jul. 2, 2019.

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 17/3496* (2013.01); *A61B 2017/3425* (2013.01); *A61B 2017/3456* (2013.01)

(58) Field of Classification Search
CPC .......... A61B 17/3423; A61B 17/00234; A61B 17/3496; A61B 17/3494; A61B 17/3498; A61B 2017/3425; A61B 2017/3456; A61B 2017/3458; A61B 2017/3427; A61B 2017/345
See application file for complete search history.

(56) References Cited

U.S. PATENT DOCUMENTS

| | | | | |
|---|---|---|---|---|
| 8,343,138 B2* | 1/2013 | Asfora | .................... | A61M 1/82 |
| | | | | 604/177 |
| 2004/0243145 A1* | 12/2004 | Bobo, Sr. | ........... | A61B 17/1695 |
| | | | | 606/129 |

* cited by examiner

*Primary Examiner* — Ashley L Fishback
(74) *Attorney, Agent, or Firm* — Riverside Law LLP

(57) ABSTRACT

The present invention provides minimally invasive subdural evacuating systems and methods of use thereof. The subdural evacuating systems include a cutting component and a rod component, wherein the rod component provides an external physical indicator that the surface of the dura mater has been reached, permitting the cutting component to accurately pierce the dura mater with minimal to no risk of damaging any adjacent anatomy.

20 Claims, 8 Drawing Sheets

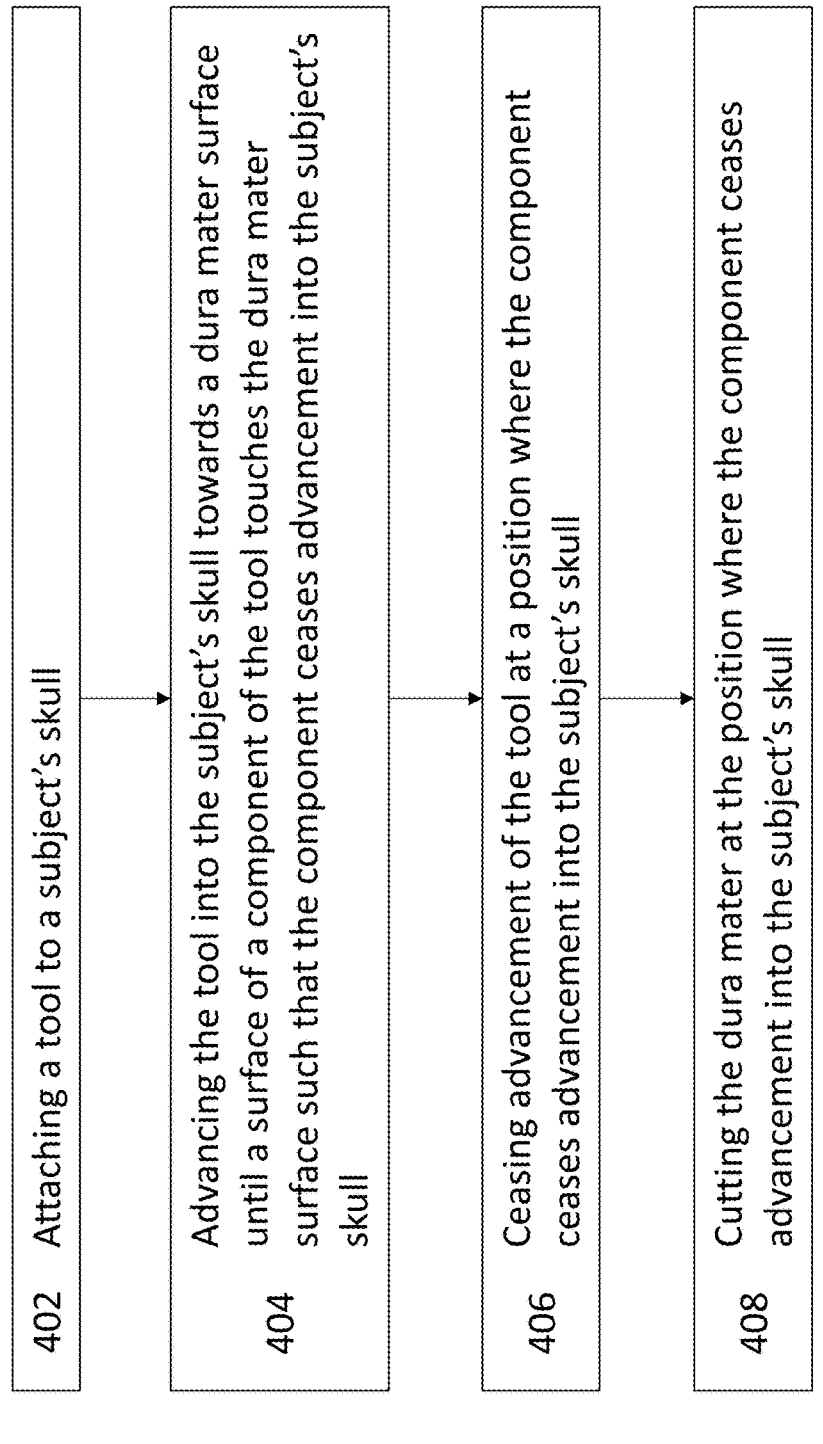

400

402    Attaching a tool to a subject's skull

404    Advancing the tool into the subject's skull towards a dura mater surface until a surface of a component of the tool touches the dura mater surface such that the component ceases advancement into the subject's skull 406    Ceasing advancement of the tool at a position where the component ceases advancement into the subject's skull 408    Cutting the dura mater at the position where the component ceases advancement into the subject's skull

FIG. 4

MINIMALLY INVASIVE SUBDURAL EVACUATING SYSTEM

CROSS-REFERENCE TO RELATED APPLICATIONS

This application is a divisional of U.S. patent application Ser. No. 17/376,645, filed Jul. 15, 2021, now allowed, which is a continuation of U.S. patent application Ser. No. 16/917,166, filed Jun. 30, 2020, now issued, which is entitled to priority under 35 U.S.C. § 119(e) to U.S. Provisional Patent Application No. 62/869,653, filed Jul. 2, 2019, the contents of which are each incorporated by reference herein in their entirety.

BACKGROUND OF THE INVENTION

Subdural hematomas continue to be a challenging set of pathology for neurosurgeons given today's aging population. Chronic subdural hematomas have the option to be drained in the operating room with small burr holes, a craniotomy, or at the bedside with newer systems, including the Medtronic Subdural Evacuating Port System (SEPS). However, one problem associated with newer systems is the inability to ascertain whether the dura has been opened or opened enough to allow for the evacuation of chronic subdural blood. For these new systems, it is often recommended to use a needle or small knife to open the dura blindly. Commonly, another SEPS has to be placed at the bedside to fix a failed one. Sometimes, a patient has to go to the operating room for a craniotomy to drain the subdural if the SEPS fails. Brain and intracranial blood vessel injuries are known to be caused by the blind passing of needles or scalpels through these existing devices.

Thus, there is a need in the art for an improved subdural evacuating system that accurately pierces the dura mater while minimizing injury. The present invention satisfies this need.

SUMMARY OF THE INVENTION

In one aspect, the present invention relates to a minimally invasive subdural evacuating system, comprising: a port having a distal threaded end and a lumen extending between a proximal opening and a distal opening; an inner cannula having a distal cutting end, a lumen extending between a proximal opening and a distal opening, and an outer diameter sized to fit within the lumen of the port; and an indicator rod having a distal blunt end and an outer diameter sized to fit within the lumen of the inner cannula.

In one embodiment, the indicator rod is slidable between a proximal position and a distal position within the lumen of the inner cannula and is maintained in a distal position by a spring force. In one embodiment, the system further comprises a depth stopper ring threadably engaged to a threaded proximal end of the inner cannula, wherein the depth stopper ring has a diameter greater than the proximal opening of the port.

In one embodiment, the inner cannula has a height that is greater than a height of the port. In one embodiment, the indicator rod has a height that is greater than a height of the inner cannula. In one embodiment, the port comprises a self-tapping distal end. In one embodiment, the port comprises one or more pin slots extending from an outer surface to the port lumen. In one embodiment, the inner cannula comprises an outer surface having one or more grooves embedded near a proximal end.

In one embodiment, the system further comprises one or more pins sized to extend through a port pin slot and into an inner cannula groove, such that inner cannula movement within the port lumen between a proximal position and a distal position is guided by a pin sliding through an inner cannula groove. In one embodiment, the inner cannula is maintained in a proximal position by a spring force. In one embodiment, the groove is sloped, such that inner cannula movement within the port lumen between the proximal position and the distal position is accompanied by rotational movement.

In one embodiment, the cutting end of the inner cannula comprises one or more hooks or barbs. In one embodiment, the inner cannula comprises an outer surface having one or more depth markers embedded near a proximal end. In one embodiment, the system further comprises a cannula guide having a lumen extending between a proximal opening and a distal opening, wherein the distal opening is releasably engageable to a proximal end of the port. In one embodiment, the cannula guide lumen is sized to fit the outer diameter of the inner cannula.

In one aspect, the present invention relates to a method of piercing a dura mater, comprising the steps of: attaching a tool to a subject's skull; advancing the tool into the subject's skull towards a dura mater surface until a surface of a component of the tool touches the dura mater surface such that the component ceases advancement into the subject's skull; ceasing advancement of the tool at a position where the component ceases advancement into the subject's skull; and cutting the dura mater at the position where the component ceases advancement into the subject's skull.

In one embodiment, the tool is a subdural evacuating system having a distal threaded end and an inner cannula having a distal cutting end, the component is an indicator rod, and the surface of the component is a blunt distal end of the indicator rod, wherein the inner cannula is positioned within a lumen of the port, the indicator rod is positioned within a lumen of the inner cannula, the inner cannula cutting end is substantially flush with the port threaded end, and the indicator rod blunt end extends for a distance beyond the port threaded end.

In one embodiment, the port threaded end is screwed into a burr hole in a subject's skull until the indicator rod blunt end touches a dura mater surface and is pushed out of a proximal end of the inner cannula by the distance, such that the indicator rod ceases advancement into the subject's skull. In one embodiment, the dura mater is cut by actuating the inner cannula to penetrate the dura mater surface with the cutting end. In one embodiment, the burr hole is formed by a drill bit drilling through the lumen of the port such that the port forms a physical stop for the drill bit.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 1A is a side view of the system with an indicator rod primed, exposing a distal blunt end. FIG. 1B is a cross-sectional side view of the system. FIG. 1C is a magnified view of the proximal end of an inner cannula. FIG. 1D is a magnified view of the distal end of an inner cannula. FIG. 1E is a side view of the system with an actuated indicator rod. FIG. 1F is a side view of the system with an actuated inner cannula.

FIG. 2A is a side view of the system. FIG. 2B is a cross-sectional side view of the system. FIG. 2C is a magnified view of the proximal end of an inner cannula. FIG. 2D is a top-down view of the system.

FIG. 3A is a side view of the system adjacent to a subdural port. FIG. 3B is a cross-sectional side view of the system engaged to a subdural port. FIG. 3C is a side view of the system with an actuated indicator rod. FIG. 3D is a side view of the system with an actuated inner cannula.

FIG. 4 is a flowchart of an exemplary method of piercing a dura mater.

DETAILED DESCRIPTION

Figures 1A, 1B:
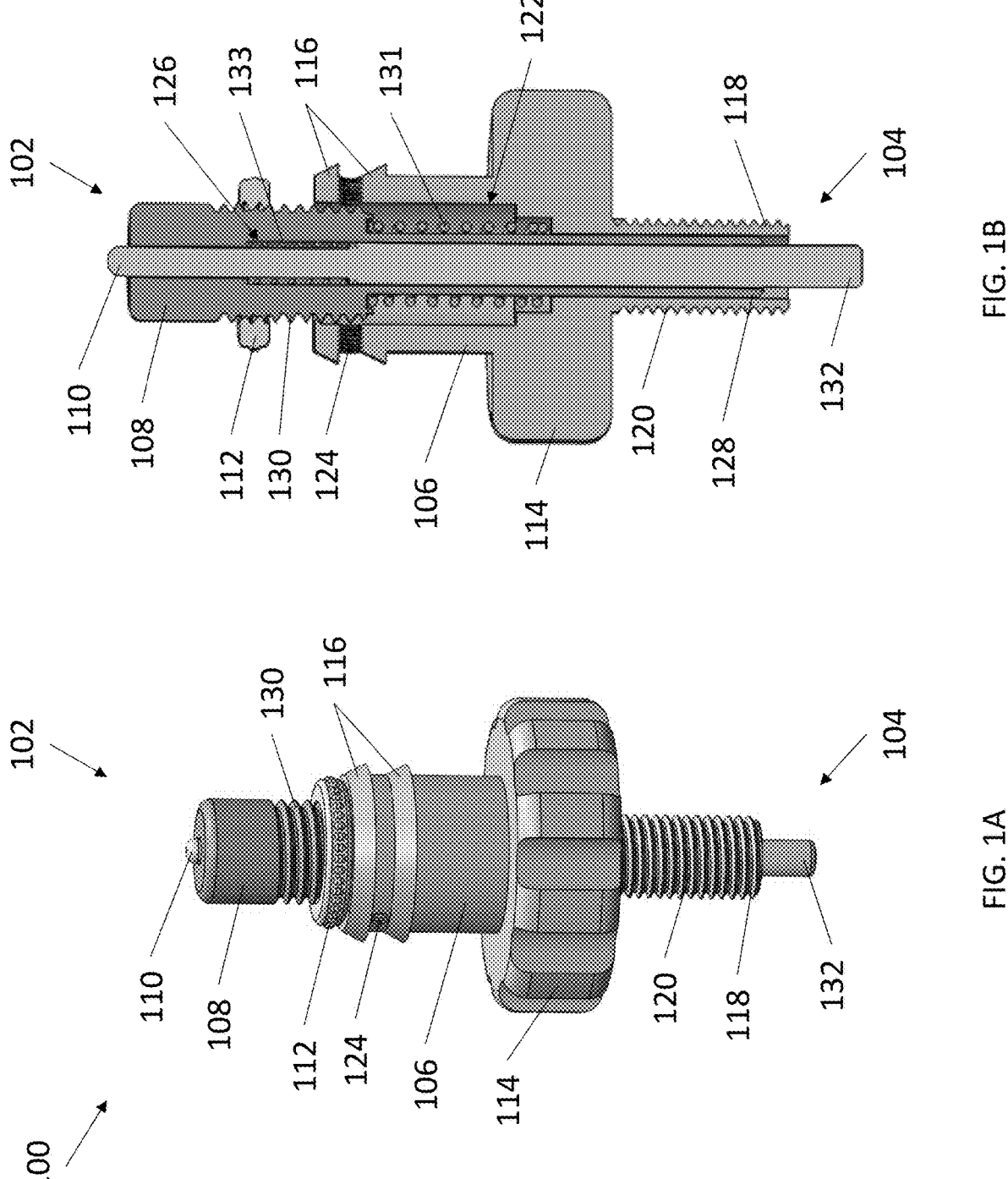
FIG. 1A through FIG. 1F depict an exemplary subdural evacuating system.
Figures 1C, 1D:
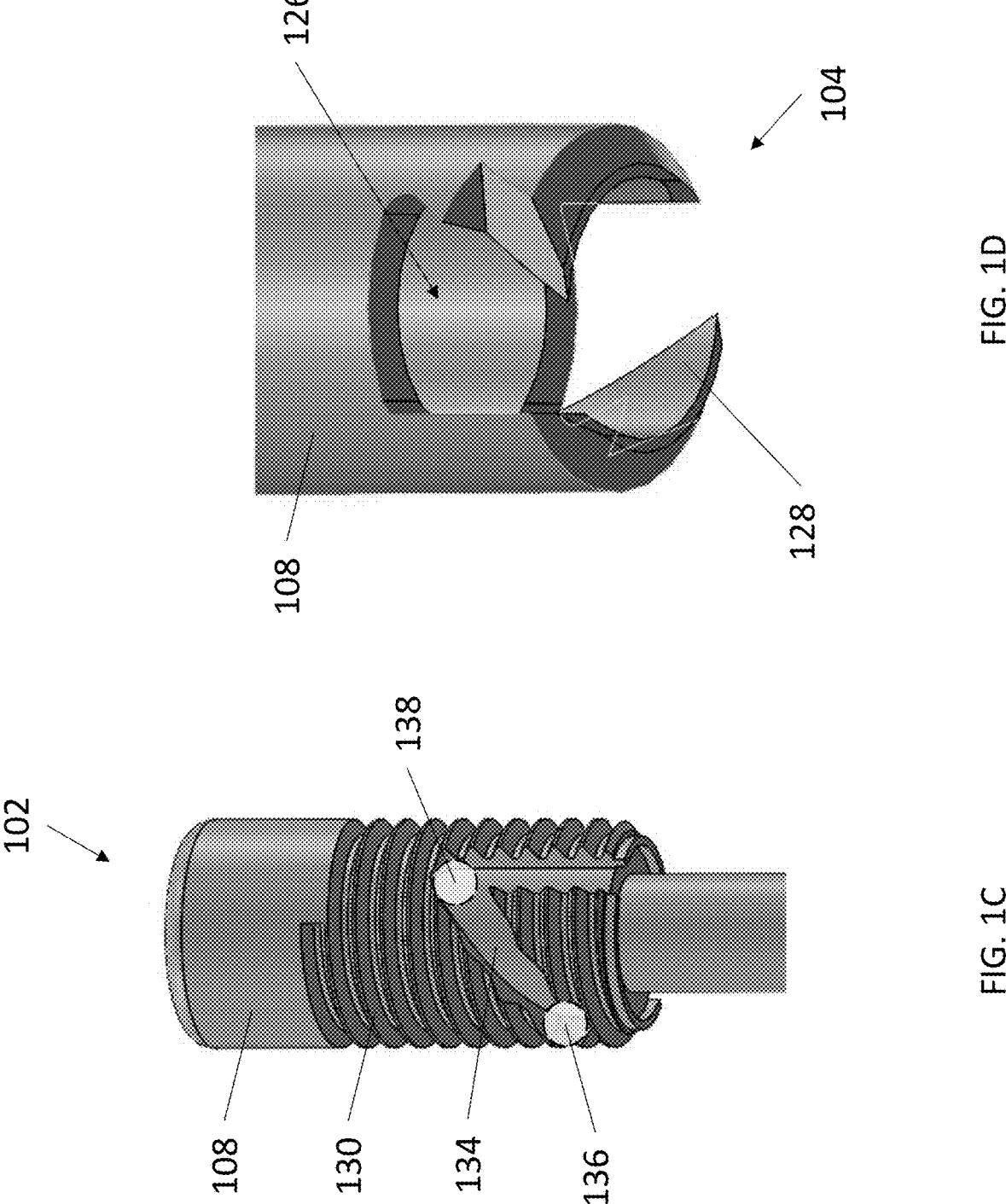

The present invention provides minimally invasive subdural evacuating systems and methods of use thereof. The subdural evacuating systems include a cutting component and a rod component, wherein the rod component provides an external physical indicator that the surface of the dura mater has been reached, permitting the cutting component to accurately pierce the dura mater with minimal to no risk of damaging any adjacent anatomy.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Minimally Invasive Subdural Evacuating System

Referring now to FIG. 1A through FIG. 1F, an exemplary subdural evacuating system 100 is depicted. System 100 has a proximal end 102 and a distal end 104, and comprises port 106, inner cannula 108, indicator rod 110, and depth stopper 112. Port 106 comprises a substantially cylindrical body having an exterior grip 114, one or more flanges 116 at a proximal end, and an anchor screw 118 having threads 120 at a distal end. Port 106 further comprises a lumen 122 extending from a proximal opening and a distal opening, as well as one or more pin slots 124 positioned at a proximal end, each pin slot 124 extending from an outer surface of port 106 into lumen 122. Each pin slot 124 is sized to accept a pin (not pictured).

Inner cannula 108 comprises a substantially elongate cylindrical body having a lumen 126 extending from a proximal opening and a distal opening. Inner cannula 108 has a height that is greater than a height of port 106 and an outer diameter that is sized to fit substantially flush within lumen 122 of port 106, such that inner cannula 108 is movable in proximal and distal directions within lumen 122. Inner cannula 108 further comprises a cutting end 128 at a distal tip (visible in greater detail in FIG. 1D) and thread 130 at a proximal end. In some embodiments, cutting end 128 comprises one or more hooked or barbed tips, wherein the hooked or barbed tips are configured to grip a dura mater surface and enables the dura mater surface to be tented and held against the distal tip of port 106. Visible in FIG. 1C, inner cannula 108 comprises at least one groove 134 cutting through thread 130. Each groove 134 is sized to fit a pin threaded through a pin slot 124. Groove 134 comprises a first stop 136 and a second stop 138, such that inner cannula 108 can be actuated to guide a pin between first stop 136 and second stop 138 and thereby transition inner cannula 108 between a proximal position at first stop 136 and a distal position at second stop 138. In certain embodiments, a spring force is provided between port 106 and inner cannula 108 to maintain the positioning of a pin in first stop 136, placing inner cannula 108 in a proximal position. The spring force can be provided by any suitable mechanism, such as a coil spring, a disc spring, a wave spring, a gas spring, and the like. For example, FIG. 1B depicts an exemplary inner cannula spring 131 positioned between a rim of the proximal end of inner cannula 108 and a rim of lumen 122 to push the two away from each other.

Indicator rod 110 comprises a substantially elongate rod-like body having a height that is greater than a height of inner cannula 108 and an outer diameter that is sized to fit substantially flush within lumen 126 of inner cannula 108, such that indicator rod 110 is movable in proximal and distal directions within lumen 126. Indicator rod 110 further comprises an atraumatic blunt end 132. In certain embodiments, a spring force is provided between inner cannula 108 and indicator rod 110 to maintain the positioning of indicator rod 110 in a distal position. The spring force can be provided by any suitable mechanism, such as a coil spring, a disc spring, a wave spring, a gas spring, and the like. For example, FIG. 1B depicts an exemplary indicator rod spring 133 attached to a rim of lumen 126 and a proximal edge of indicator rod 110 to push the two away from each other. In some embodiments, the spring force is adjustable to vary the position of indicator rod 110.

Depth stopper 112 comprises a substantially ring-like shape and has an inner threading mated to thread 130 of inner cannula 108. As described elsewhere herein, inner cannula 108 has an outer diameter that is sized to fit substantially flush within lumen 122 of port 106, such that depth stopper 112 threaded onto inner cannula 108 engages a proximal end of port 106 to control the depth at which inner cannula 108 enters lumen 122 of port 106.

The abovementioned components of system 100 work together to place a port within a cranial burr hole and to accurately pierce the dura mater with minimal risk of injury to adjacent anatomy by providing an external indicator of the position of system 100 relative to a subject's skull and dura mater. The following is a description of an exemplary mode of operating system 100. Referring to FIG. 1A, a spring force at rest maintains indicator rod 110 in a distal position such that blunt end 132 extends for a small distance out of the distal end of port 106. A spring force at rest maintains inner cannula 108 in a proximal position such that cutting end 128 is substantially flush with the distal end of port 106. As described above, the proximal position of inner cannula 108 is determined by a pin (not pictured) inserted through pin slot 124 of port 106 and into groove 134 of inner cannula 108 to rest in first stop 136, shown in FIG. 1C. Depth stopper 112 can be rotated about inner cannula 108 to select a depth of penetration, as shown in FIG. 1B. With cutting end 128 substantially flush with the distal end of port 106, the distance between depth stopper 112 and the proximal end of port 106 approximates the depth at which cutting end 128 penetrates beyond the distal end of port 106 when inner cannula 108 is actuated.

Figure 1F:
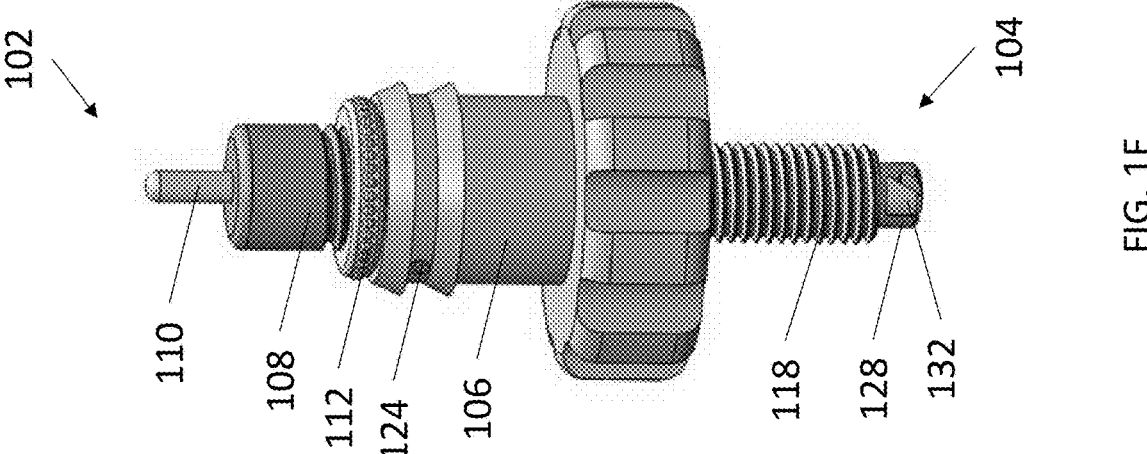
Figure 1E:
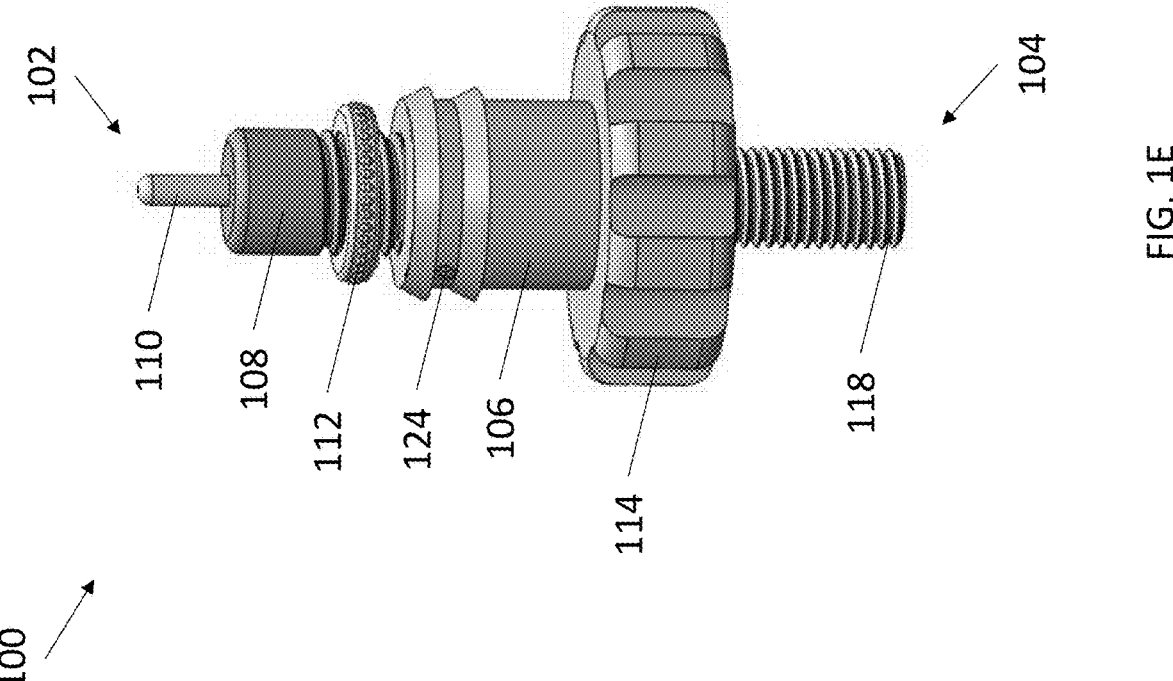

Once depth stopper 112 has been rotated to a selected depth of penetration, system 100 can be inserted into a subject's skull by screwing anchor screw 118 into a cranial burr hole. As system 100 is advanced deeper into a cranial burr hole with each turn of port 106, blunt end 132 of indicator rod 110 eventually touches the surface of an underlying dura mater and is pushed in a proximal direction as system 100 is further advanced into a cranial burr hole. The proximal movement of indicator rod 110 thereby provides a physical indicator of the relative distance between the distal end of port 106 and the dura mater surface. Referring now to FIG. 1E, the insertion of system 100 into a cranial burr hole has brought the distal end of port 106 flush against the dura mater surface, which is demonstrated by indicator rod 110 being pushed out of the proximal end of inner cannula 108. In FIG. 1F, inner cannula 108 is actuated to penetrate the dura mater surface below the distal end of port 106. In some embodiments, actuating inner cannula 108 provides both a twisting movement and a piercing movement to penetrate the dura mater surface. Referring back to FIG. 1C, actuation of inner cannula 108 is guided by a pin moving through groove 134. By moving pin from first stop 136 to second stop 138, actuating inner cannula 108 rotates to produce a twisting movement and advances in a distal direction to produce a piercing movement. After the dura mater surface has been penetrated, inner cannula 108, indicator rod 110, and depth stopper 112 may be removed from system 100, leaving port 106 in a subject's skull for further operations. In some embodiments, inner cannula 108 or an alternate inner cannula can be reintroduced into port 106, such as to macerate a clot or to clear some other obstruction.

Referring now to FIG. 2A through FIG. 2D, an exemplary subdural evacuating system 200 is depicted. System 200 has a proximal end 202 and a distal end 204, and comprises port 206, inner cannula 208, indicator rod 210, and depth stopper 212. Port 206 comprises a substantially cylindrical body having an exterior grip 214, one or more flanges 216 at a proximal end, and an anchor screw 218 having threads 220 at a distal end. Port 206 further comprises a lumen 222 extending from a proximal opening and a distal opening, as well as one or more pin slots 224 positioned at a proximal end, each pin slot 224 extending from an outer surface of port 206 into lumen 222. Each pin slot 224 is sized to accept a pin (not pictured).

Figures 2A, 2B:
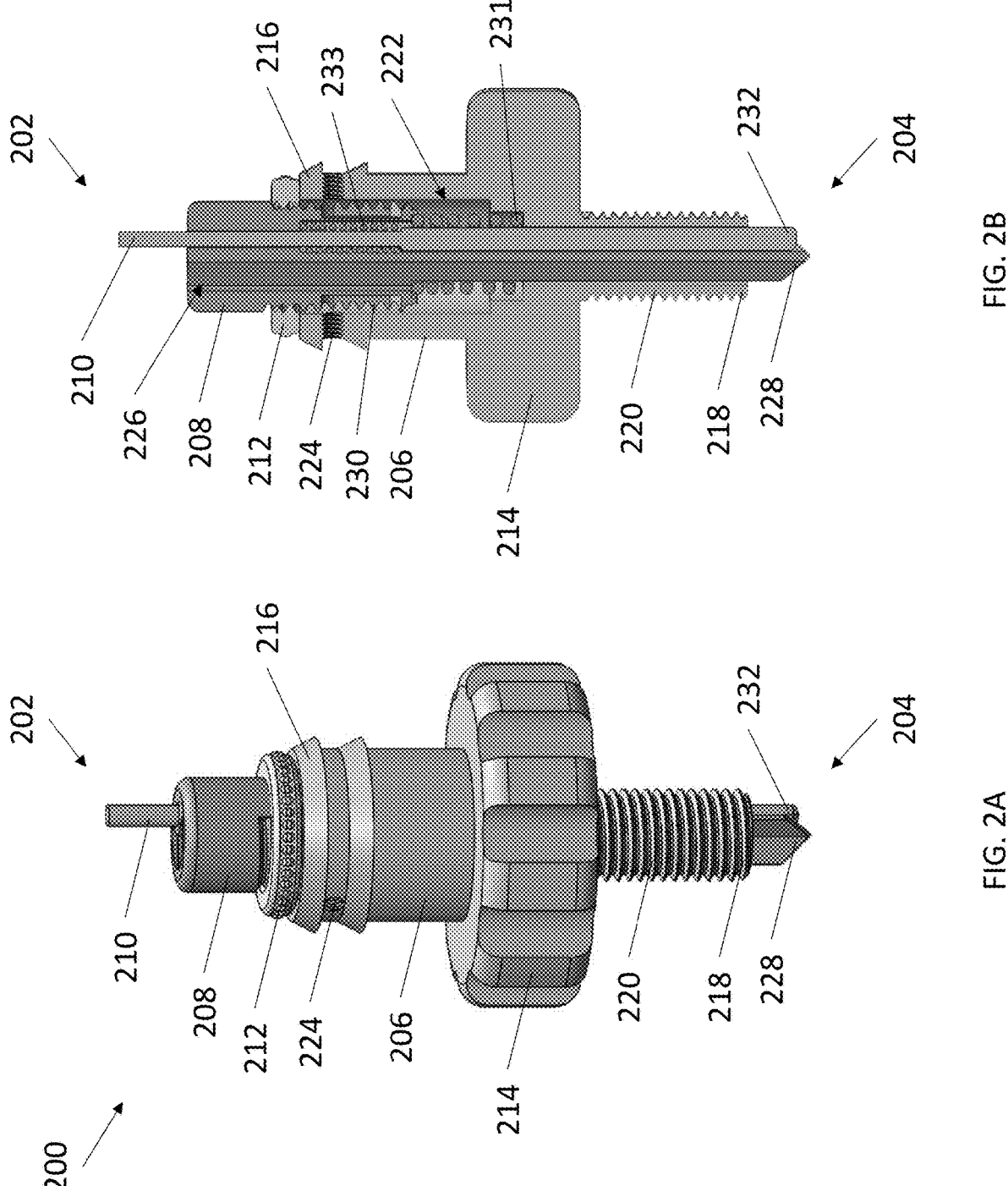
FIG. 2A through FIG. 2D depict another exemplary subdural evacuating system.
Figures 2C, 2D:
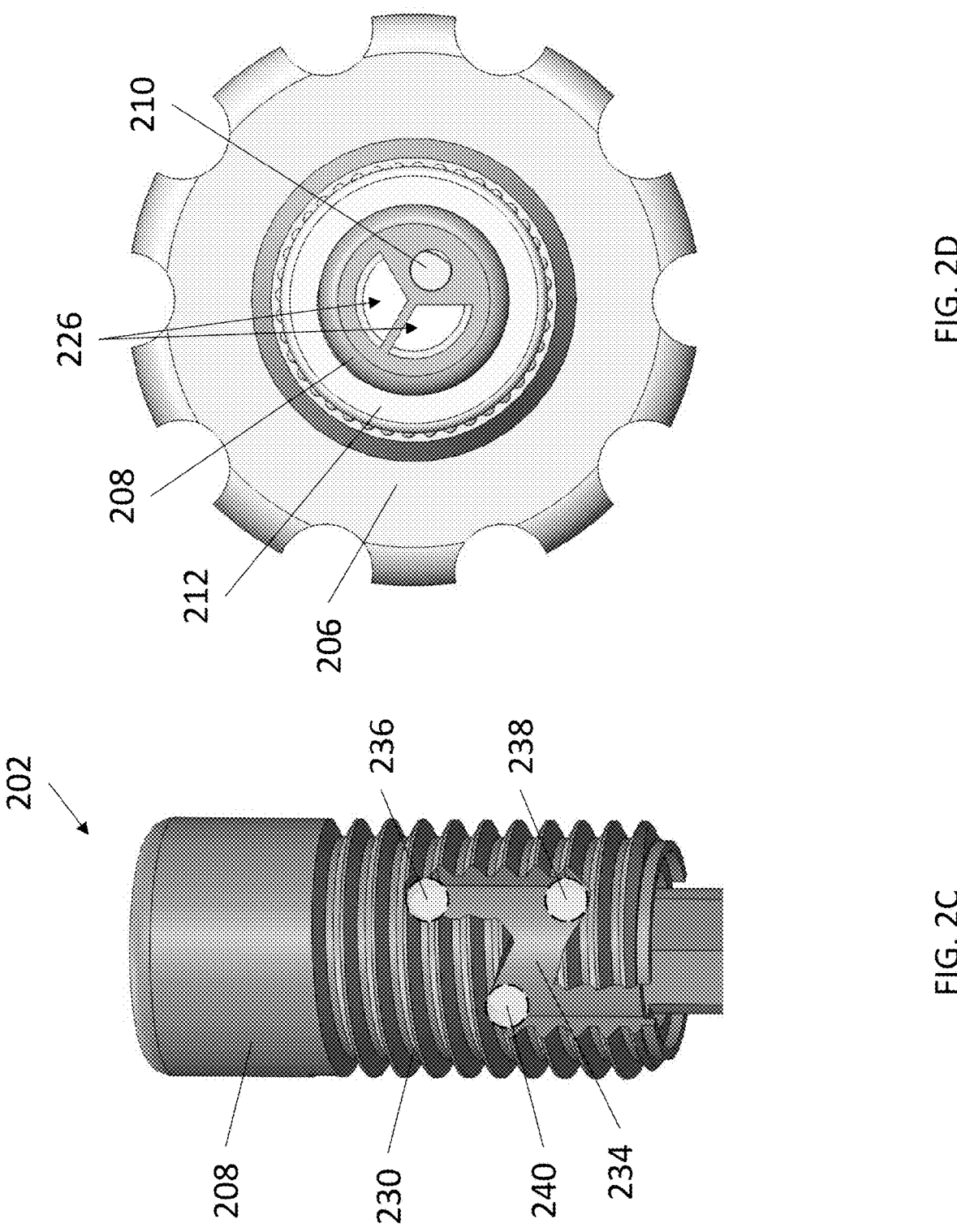

Inner cannula 208 comprises a substantially elongate cylindrical body having at least one lumen 226 extending from a proximal opening and a distal opening. The at least one lumen 226 permits draining of fluids during and after insertion of system 200 (visible in FIG. 2D). Inner cannula 208 has a height that is greater than a height of port 206 and an outer diameter that is sized to fit substantially flush within lumen 222 of port 206, such that inner cannula 208 is movable in proximal and distal directions within lumen 222. Inner cannula 208 further comprises a piercing end 228 at a distal tip and thread 230 at a proximal end. Visible in FIG. 2C, inner cannula 208 comprises at least one groove 234 cutting through thread 230. Each groove 234 is sized to fit a pin threaded through a pin slot 224. Groove 234 comprises a first stop 236, a second stop 238, and a third stop 240, such that inner cannula 208 can be actuated to guide a pin between first stop 236, and second stop 238 and thereby transition inner cannula 208 between a proximal position at second stop 238 and a distal position at first stop 238. In certain embodiments, a spring force is provided between port 206 and inner cannula 208 to maintain the positioning of a pin in second stop 238, placing inner cannula 108 in a proximal position. The spring force can be provided by any suitable mechanism, such as a coil spring, a disc spring, a wave spring, a gas spring, and the like. For example, FIG. 2B depicts an exemplary inner cannula spring 231 positioned between a rim of the proximal end of inner cannula 208 and a rim of lumen 222 to push the two away from each other.

Indicator rod 210 comprises a substantially elongate rod-like body having a height that is greater than a height of inner cannula 208 and an outer diameter that is sized to fit substantially flush within a lumen 226 of inner cannula 208, such that indicator rod 210 is movable in proximal and distal directions within a lumen 226. Indicator rod 210 further comprises an atraumatic blunt end 232. In certain embodiments, a spring force is provided between inner cannula 208 and indicator rod 210 to maintain the positioning of indicator rod 210 in a distal position. The spring force can be provided by any suitable mechanism, such as a coil spring, a disc spring, a wave spring, a gas spring, and the like. For example, FIG. 2B depicts an exemplary indicator rod spring 233 attached to a rim of lumen 226 and a proximal edge of indicator rod 210 to push the two away from each other. In some embodiments, the spring force is adjustable to vary the position of indicator rod 210.

Depth stopper 212 comprises a substantially ring-like shape and has an inner threading mated to thread 230 of inner cannula 208. As described elsewhere herein, inner cannula 208 has an outer diameter that is sized to fit substantially flush within lumen 222 of port 206, such that depth stopper 212 threaded onto inner cannula 208 engages a proximal end of port 206 to control the depth at which inner cannula 208 enters lumen 222 of port 206.

The abovementioned components of system 200 work together to place a port within a cranial burr hole and to accurately pierce the dura mater with minimal risk of injury to adjacent anatomy by providing an external indicator of the position of system 200 relative to a subject's skull and dura mater. The following is a description of an exemplary mode of operating system 200. Similar to system 100 depicted in FIG. 1A, a spring force at rest maintains indicator rod 210 in a distal position such that blunt end 232 extends for a small distance out of the distal end of port 206. A spring force at rest maintains inner cannula 208 in a proximal position such that cutting end 228 is substantially flush with the distal end of port 206. As described above, the proximal position of inner cannula 208 is determined by a pin (not pictured) inserted through pin slot 224 of port 206 and into groove 234 of inner cannula 208 to rest in second stop 238, shown in FIG. 2C. Depth stopper 212 can be rotated about inner cannula 208 to select a depth of penetration, similar to system 100 depicted in FIG. 1E. With cutting end 228 substantially flush with the distal end of port 206, the distance between depth stopper 212 and the proximal end of port 206 approximates the depth at which cutting end 228 penetrates beyond the distal end of port 206 when inner cannula 208 is actuated.

Once depth stopper 212 has been rotated to a selected depth of penetration, system 200 can be inserted into a subject's skull by screwing anchor screw 218 into a cranial burr hole. As system 200 is advanced deeper into a cranial burr hole with each turn of port 206, blunt end 232 of indicator rod 210 eventually touches the surface of an underlying dura mater and is pushed in a proximal direction as system 200 is further advanced into a cranial burr hole. The proximal movement of indicator rod 210 thereby provides a physical indicator of the relative distance between the distal end of port 206 and the dura mater surface. Similar to system 100 depicted in FIG. 1E, when the insertion of system 200 into a cranial burr hole brings the distal end of port 206 flush against the dura mater surface, indicator rod 210 will have been pushed out of the proximal end of inner cannula 208. In FIG. 2A, inner cannula 208 is actuated to penetrate the dura mater surface below the distal end of port 206. In some embodiments, actuating inner cannula 208 provides a piercing movement to penetrate the dura mater surface. Referring back to FIG. 2C, actuation of inner cannula 208 is guided by a pin moving through groove 234. By moving pin from second stop 238 to first stop 236, actuating inner cannula 208 advances in a distal direction to produce a piercing movement. After the dura mater surface has been penetrated, inner cannula 208, indicator rod 210, and depth stopper 212 may be removed from system 200, leaving port 206 in a subject's skull for further operations. In some embodiments, inner cannula 208 or an alternate inner cannula can be reintroduced into port 206, such as to macerate a clot or to clear some other obstruction.

Referring now to FIG. 3A through FIG. 3D, an exemplary subdural evacuating system 300 is depicted. System 300 has a proximal end 302 and a distal end 304, and comprises port 306, inner cannula 308, indicator rod 310, and cannula holder 312. Port 306 comprises a substantially cylindrical body having an exterior grip 314, one or more flanges 316 at a proximal end, and an anchor screw 318 having threads 320 at a distal end. Port 306 further comprises a lumen 322 extending from a proximal opening and a distal opening.

Cannula guide 312 comprises a substantially cylindrical body having a lumen 334 extending between a proximal opening and a distal opening. Cannula guide 312 releasably attaches to a proximal end of port 306 by way of at least one snap arm 336 engaging one or more flanges 316. In some embodiments, cannula guide 312 comprises one or more pin slots 338 positioned at a proximal end, each pin slot 338 extending from an outer surface of cannula guide 312 into lumen 334. Each pin slot 338 is sized to accept a pin (not pictured).

Figures 3A, 3B:
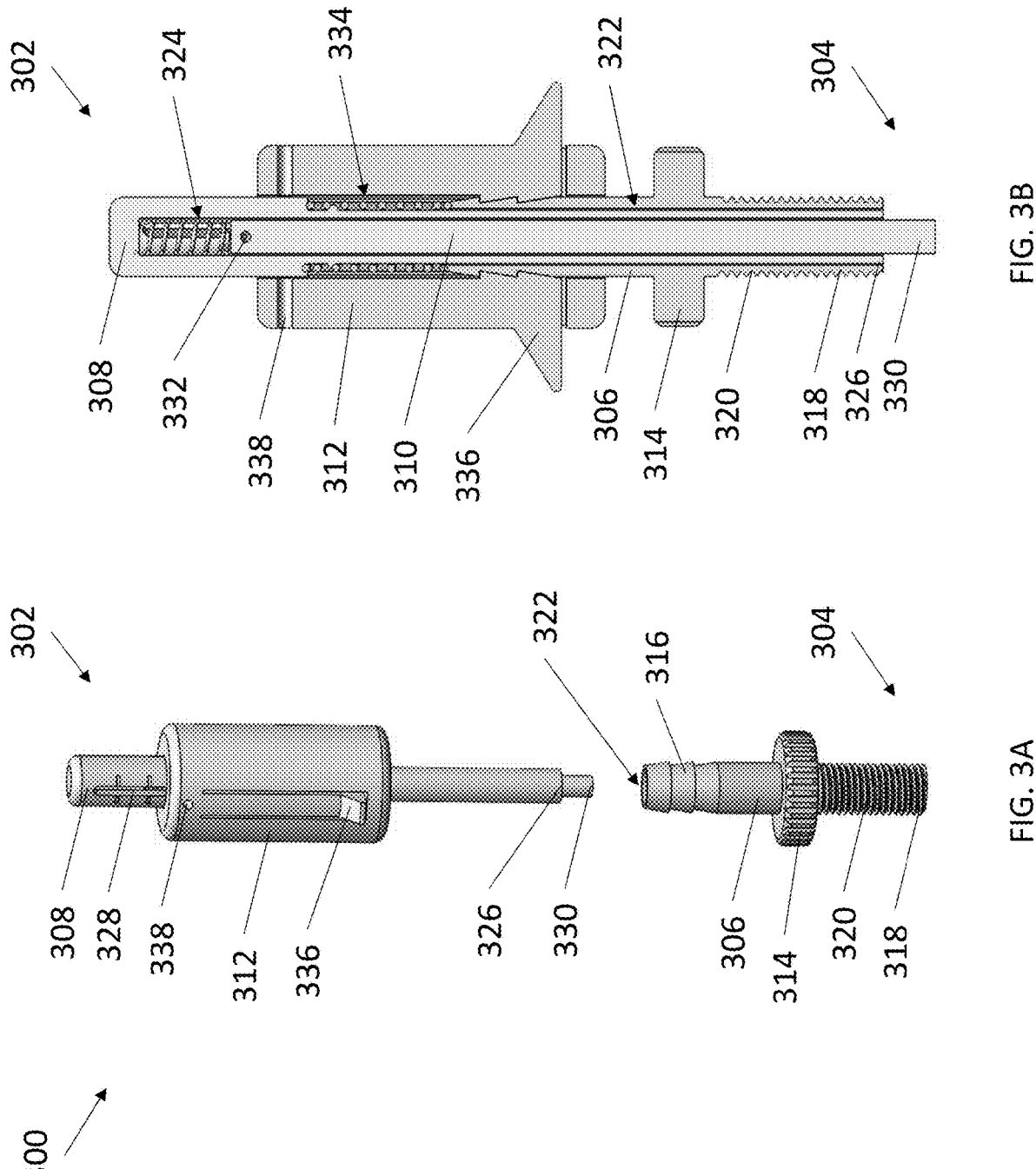
FIG. 3A through FIG. 3D depict another exemplary subdural evacuating system.

Inner cannula 308 comprises a substantially elongate cylindrical body having a height that is greater than a height of port 306 and a height of cannula guide 318 and a lumen 324 extending from a proximal end and a distal opening. Inner cannula 308 has an outer diameter that is sized to fit substantially flush within lumen 334 of cannula guide 312 and lumen 322 of port 306, such that inner cannula 308 is movable in proximal and distal directions within lumen 334 and lumen 322. Inner cannula 308 further comprises a piercing end 326 at a distal tip. Visible in FIG. 3C, inner cannula 308 comprises one or more slots 328 and depth markers on an outer surface, such as first stop 340 and second stop 342. The one or more slots 328 are sized to fit a pin inserted through pin slot 338, such that inner cannula 308 has an actuation range between a proximal position and a distal position as determined by the pin traveling through the one or more slots 328. In certain embodiments, a spring force is provided between port 306 and inner cannula 308 to maintain the positioning of inner cannula 308 in a proximal position. The spring force can be provided by any suitable mechanism, such as a coil spring, a disc spring, a wave spring, a gas spring, and the like. For example, FIG. 3B depicts an exemplary inner cannula spring 331 positioned between a rim of the proximal end of inner cannula 308 and a proximal rim of port 306 to push the two away from each other.

Indicator rod 310 comprises a substantially elongate rod-like body having an outer diameter that is sized to fit substantially flush within lumen 324 of inner cannula 308, such that indicator rod 310 is movable in proximal and distal directions within lumen 324. Indicator rod 310 further comprises an atraumatic blunt end 330. In some embodiments, indicator rod 310 comprises a pin slot 332 at a proximal end, wherein a pin (not pictured) inserted into pin slot 332 and slot 328 determines the actuation range of indicator rod 310. In certain embodiments, a spring force is provided between inner cannula 308 and indicator rod 310 to maintain the positioning of indicator rod 310 in a distal position. The spring force can be provided by any suitable mechanism, such as a coil spring, a disc spring, a wave spring, a gas spring, and the like. For example, FIG. 3B depicts an exemplary indicator rod spring 333 attached to a proximal end of lumen 324 and a proximal tip of indicator rod 310 to push the two away from each other. In some embodiments, the spring force is adjustable to vary the position of indicator rod 310.

The abovementioned components of system 300 work together to place a port within a cranial burr hole and to accurately pierce the dura mater with minimal risk of injury to adjacent anatomy by providing an external indicator of the position of system 300 relative to a subject's skull and dura mater. The following is a description of an exemplary mode of operating system 300. Referring to FIG. 3B, a spring force at rest maintains indicator rod 310 in a distal position such that blunt end 330 extends for a small distance out of the distal end of port 306. A spring force at rest maintains inner cannula 308 in a proximal position such that cutting end 326 is substantially flush with the distal end of port 306. As described above, the proximal position of inner cannula 308 is determined by a pin (not pictured) inserted through pin slot 338 of cannula guide 312 and into slot 328 of inner cannula 308. With cutting end 326 substantially flush with the distal end of port 306, the distance between a first depth marker, such as first stop 340, and a second depth marker, such as second stop 342, approximates the depth at which cutting end 326 penetrates beyond the distal end of port 306 when inner cannula 308 is actuated.

Figure 3D:
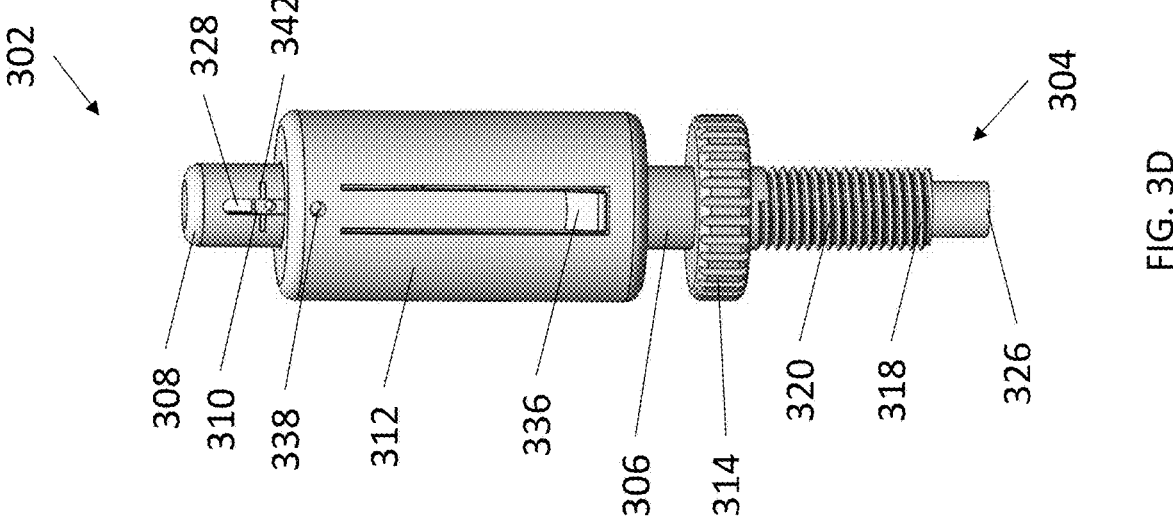
Figure 3C:
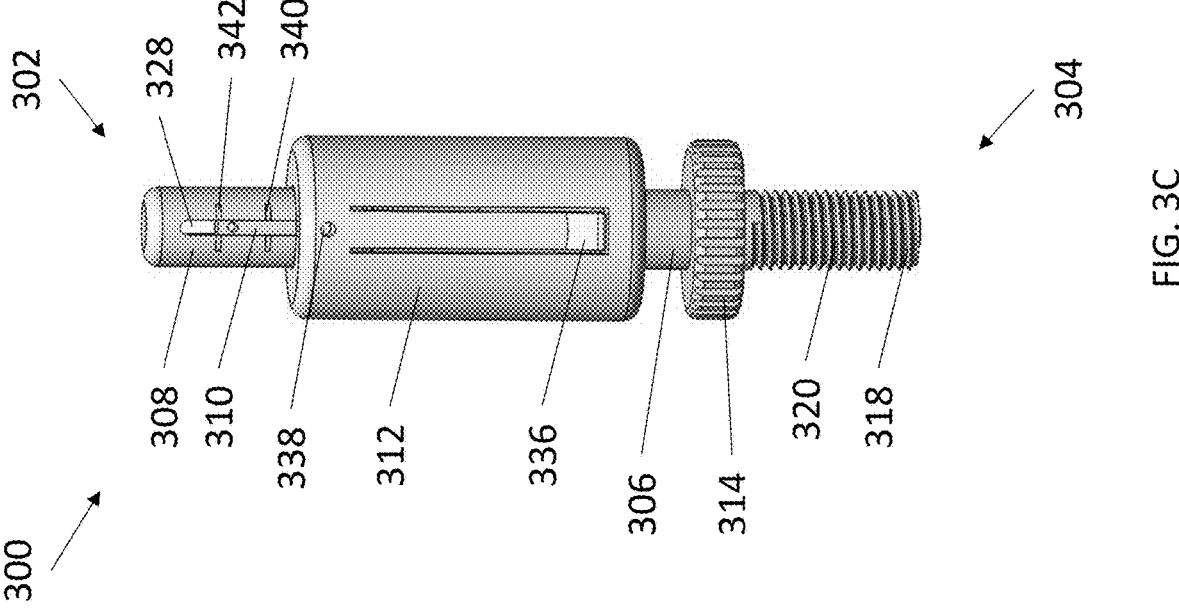

Once indicator rod 310 is aligned with a selected depth marker, system 300 can be inserted into a subject's skull by screwing anchor screw 318 into a cranial burr hole. As system 300 is advanced deeper into a cranial burr hole with each turn of port 306, blunt end 330 of indicator rod 310 eventually touches the surface of an underlying dura mater and is pushed in a proximal direction as system 300 is further advanced into a cranial burr hole. The proximal movement of indicator rod 310 thereby provides a physical indicator of the relative distance between the distal end of port 306 and the dura mater surface. Referring to FIG. 3C, when the insertion of system 300 into a cranial burr hole brings the distal end of port 306 flush against the dura mater surface, indicator rod 310 will have been pushed from a first depth marker to a second depth marker on inner cannula 308. In FIG. 3D, inner cannula 308 is actuated to penetrate the dura mater surface below the distal end of port 306. In some embodiments, actuating inner cannula 308 provides a twisting or piercing movement to penetrate the dura mater surface. After the dura mater surface has been penetrated, inner cannula 308, indicator rod 310, and cannula guide 312 may be removed from system 300, leaving port 306 in a subject's skull for further operations. In some embodiments, inner cannula 308 or an alternate inner cannula can be reintroduced into port 306, such as to macerate a clot or to clear some other obstruction.

The components of the systems of the present invention can have any suitable construction. For example, while each system has been described as including a port, any commonly used cranial port may be used with the cannulas and indicator rods of the present invention. While skull thicknesses vary among subjects, typical thicknesses are between about 5 mm and 8 mm. Accordingly, ports contemplated within the present invention can have an anchor screw length of at least 5 mm. The various inner cannulas and their respective depth management mechanisms can be adjustable to match the thickness of a dura mater. While dura mater thicknesses vary among subjects, typical thicknesses are between about 3 mm and 5 mm. In either case, subjects can be imaged, such as with MRI or with a CT scan, to ascertain the actual thickness of a subject's anatomy to adjust or select components accordingly. While the ports described herein have flanges at a proximal end for connecting to drainage and vacuum tubes, any suitable connecting feature can be used, such as threading, fir tree connectors, luer locks, stepped connectors, and the like. In some embodiments, the distal end of the ports can be self-tapping to aid in insertion into a burr hole.

The components of the systems of the present invention can be constructed from any suitable material, including but not limited to metals and polymers, such as stainless steel, titanium, aluminum, polyether ether ketone (PEEK), polyethylenes, polyvinyls, polyurethanes, polyamides, polycarbonates, and the like. In some embodiments, certain components or portions of certain components can be constructed from a transparent or translucent material. The components and systems can be made using any suitable method known in the art. The method of making may vary depending on the materials used. For example, devices substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

Methods of Use

The present invention also includes methods of accurately piercing the dura mater. As described elsewhere herein, the present invention provides subdural evacuating systems that comprise a port component and an indicator component, wherein the indicator component detects when physical contact has been made with a dura mater. The methods thereby provide steps of accurately piercing the dura mater by providing an indicator of the position of the systems relative to a subject's skull and dura mater, and subsequently for placing a port within a cranial burr hole with minimal risk of injury to adjacent anatomy.

Referring now to FIG. 4, an exemplary method 400 of piercing a dura mater is depicted. Method 400 beings with step 402, wherein a tool is attached to a subject's skull. In step 404, the tool is advanced into the subject's skull towards a dura mater surface until a surface of a component of the tool touches the dura mater surface such that the component ceases advancement into the subject's skull. In step 406, advancement of the tool is ceased at a position where the component ceases advancement into the subject's skull. In step 408, the dura mater is cut at the position where the component ceases advancement into the subject's skull.

In some embodiments, the tool is a subdural evacuating system as described elsewhere herein. The system can comprise a port having a distal threaded end and an inner cannula having a distal cutting end, the component is an indicator rod, and the surface of the component is a blunt distal end of the indicator rod, wherein the inner cannula is positioned within a lumen of the port, the indicator rod is positioned within a lumen of the inner cannula, the inner cannula cutting end is substantially flush with the port threaded end, and the indicator rod blunt end extends for a distance beyond the port threaded end. In some embodiments, the port threaded end is screwed into a burr hole in a subject's skull until the indicator rod blunt end touches a dura mater surface and is pushed out of a proximal end of the inner cannula by the distance, such that the indicator rod ceases advancement into the subject's skull. In some embodiments, the dura mater is cut by actuating the inner cannula to penetrate the dura mater surface with the cutting end. In some embodiments, the inner cannula and indicator rod are removed from the port to leave behind the port in the subject's skull.

In some embodiments, the method includes a step of forming a burr hole in a subject's skull. The burr hole can be formed using a drill, wherein a drill bit is guided through a port component of the subdural evacuating system. The port component can accurately position the drill bit at a desired site to form the burr hole. In certain cases, the drill bit can "bite" into bone and suddenly plunge in deeper than desired, causing inadvertent injury. The port component can also act as a physical stop, preventing the drill bit from drilling deeper than intended. The position of the drill bit can be adjusted relative to the height of the port component to control the depth of drilling. For example, the drill bit can be inserted into the lumen of the port component until the port meets a drill chuck. The drill bit can then be adjusted within the drill chuck until the drill bit end protrudes from the lumen of the port component by a distance that approximates the thickness of a subject's skull.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of piercing a dura mater, comprising the steps of:
    advancing an apparatus into a subject's skull through a port towards a dura mater surface until a surface of a component of the apparatus touches the dura mater surface such that the component ceases advancement into the subject's skull;
    ceasing advancement of the apparatus at a position where the component ceases advancement into the subject's skull; and
    indexing the position of the apparatus relative to the dura mater surface such that accurate cutting of the dura mater surface is permitted with minimal to no risk of damaging any adjacent anatomy.

2. The method of claim 1, wherein the apparatus being advanced into the subject's skull comprises:
    a subdural evacuating system having a cannula comprising a substantially elongate body and a distal cutting end;
    a position indicator configured to indicate a position of the cutting end in relation to a dura mater; and
    a depth stop configured to control a depth of the cutting end in relation to a subject's skull and dura mater.

3. The method of claim 2, wherein:
    the apparatus is inserted into the port in the subject's skull until the position indicator
    indicates that the cutting end is in proper relation to the dura mater to be cut, and the depth stop is activated to select a depth of penetration.

4. The method of claim 3, wherein:
    the dura mater is cut by actuating the cannula to penetrate the dura mater surface with the cutting end.

5. The method of claim 4, further comprising the step of:
    draining fluid from the region below the dura mater surface with the cannula.

6. The method of claim 4, further comprising the steps of:
    deactivating the cannula; and
    draining fluid from the region below the dura mater surface with the cannula.

7. The method of claim 4, further comprising the step of:
    deactivating the cannula;
    removing the cannula from the port;
    inserting a second cannula into the port;
    draining fluid from the region below the dura mater surface with the second cannula.

8. The method of claim 4, wherein:
    actuating the cannula moves the cannula from a first stop to a second stop.

9. The method of claim 4, wherein:
    actuating the cannula rotates and advances the cannula in a distal direction.

10. The method of claim 9, wherein:
    actuating the cannula enables a surface of the dura mater to be tented and held against a distal tip of the port.

11. The method of claim 4, wherein:
    the apparatus is removed from the port, leaving the port in the subject's skull for further operations.

12. A method of piercing a dura mater, comprising the steps of:
    attaching a tool to a subject's skull;
    advancing the tool into the subject's skull towards a dura mater surface until a surface of a component of the tool touches the dura mater surface such that the component ceases advancement into the subject's skull;
    ceasing advancement of the tool at a position where the component ceases advancement into the subject's skull; and
    cutting the dura mater at the position where the component ceases advancement into the subject's skull.

13. The method of claim 12, wherein:
    the tool is a subdural evacuating system comprising a port having a distal threaded end and an inner cannula having a distal cutting end, the component is an indicator rod, and the surface of the component is a blunt distal end of the indicator rod, wherein the inner cannula is positioned within a lumen of the port, the indicator rod is positioned within a lumen of the inner cannula, the inner cannula cutting end is substantially flush with the port threaded end, and the indicator rod blunt end extends for a distance beyond the port threaded end.

14. The method of claim 13, wherein:
    the port threaded end is screwed into a burr hole in a subject's skull until the indicator rod blunt end touches a dura mater surface and is pushed out of a proximal end of the inner cannula by the distance, such that the indicator rod ceases advancement into the subject's skull.

15. The method of claim 14, wherein:
    the dura mater is cut by actuating the inner cannula to penetrate the dura mater surface with the cutting end.

16. The method of claim 15, wherein:
    actuating the inner cannula rotates and advances the inner cannula in a distal direction enabling a surface of the dura mater to be tented and held against a distal tip of the port.

17. The method of claim 15, further comprising the step of:
    draining fluid from the region below the dura mater surface.

18. The method of claim 17, wherein:
    the fluid is drained through one or more lumens extending through the inner cannula.

19. The method of claim 15, further comprising the steps of:
    deactivating the inner cannula;
    removing the inner cannula from the port;
    positioning a second cannula in the lumen of the port; and
    draining fluid from the region below the dura mater surface with the second cannula.

20. The method of claim 14, wherein:
    the burr hole is formed by a drill bit drilling through the lumen of the port such that the port forms a physical stop for the drill bit.

* * * * *